United States Patent [19]

Lange et al.

[11] Patent Number: 4,729,840
[45] Date of Patent: Mar. 8, 1988

[54] LUBRICANT AND FUEL ADDITIVES DERIVED FROM O,O-DIALKYLDITHIOPHOSPHORIC ACID AND A NORBORNYL REACTANT

[75] Inventors: Richard M. Lange, Euclid; William C. Tritt, South Euclid; Stephen A. DiBiase, Euclid, all of Ohio

[73] Assignee: The Lubrizol Corporation, Wickliffe, Ohio

[21] Appl. No.: 884,685

[22] Filed: Jul. 11, 1986

[51] Int. Cl.$^4$ .................................. C10M 137/10
[52] U.S. Cl. .................................. 252/46.7; 252/46.6; 252/49.3; 558/155; 558/156; 558/177; 558/190
[58] Field of Search .................. 252/46.6, 46.7; 558/190, 177, 156, 155

[56] References Cited

U.S. PATENT DOCUMENTS

| | | | |
|---|---|---|---|
| 2,644,002 | 6/1953 | Hoegberg | 260/326.5 |
| 2,767,206 | 10/1956 | Whetstone et al. | 252/46.6 |
| 3,023,209 | 2/1962 | Reese et al. | 252/46.6 |
| 3,401,175 | 9/1968 | Osborne et al. | 260/326 |
| 3,406,225 | 10/1968 | Raden | 558/177 |
| 3,803,270 | 4/1974 | Elliopulos | 558/177 |
| 3,821,322 | 6/1974 | Shepherd, Jr. | 252/46.6 |
| 3,849,473 | 11/1974 | Inamoto et al. | 260/468 G |
| 3,916,017 | 10/1975 | Shepherd, Jr. | 252/46.6 |
| 3,943,202 | 3/1976 | Beriger et al. | 558/190 |
| 3,962,105 | 6/1976 | Lange | 252/56 R |
| 4,028,258 | 6/1977 | Kablaoui | 252/46.7 |
| 4,035,488 | 7/1977 | Drabek et al. | 558/190 |
| 4,067,972 | 1/1978 | Oswald et al. | 558/190 |
| 4,080,444 | 3/1978 | Fest et al. | 558/190 |
| 4,123,526 | 10/1978 | Large et al. | 558/190 |

Primary Examiner—William R. Dixon, Jr.
Assistant Examiner—Ellen McAvoy
Attorney, Agent, or Firm—Denis A. Polyn; Karl Bozicevic; Robert A. Franks

[57] ABSTRACT

Reaction products of 5-norbornene-2,3-dicarboxylic anhydride O,O-dialkyldithiophosphate adduct of the formula

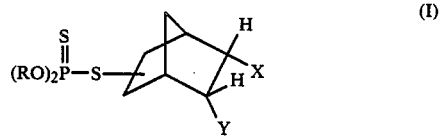

(I)

have been found to be beneficial additives for functional fluids used in the machinery of motorized vehicles. These additives are effective extreme pressure agents and antiwear agents as well as antioxidants for use in such functional fluids as lubricating oils including automatic transmission fluids and hydraulic fluids.

13 Claims, No Drawings

LUBRICANT AND FUEL ADDITIVES DERIVED FROM O,O-DIALKYLDITHIOPHOSPHORIC ACID AND A NORBORNYL REACTANT

BACKGROUND OF THE INVENTION

1. Field of the Invention

This invention relates to novel additives for functional fluids that are derived from a norbornyl reactant and O,O-dialkyldithiophosphoric acids. It has been discovered that these additives improve the extreme pressure, antiwear and antioxidant properties or functional fluids, e.g., lubricants and fuels, for use in internal combustion engines and the machinery of motorized vehicles.

2. State of the Art

O,O-Dialkyldithiophosphoric acid adducts of a norbornene reactant have been disclosed in the art. For example, in U.S. Pat. No. 3,023,209, various dialkyldithiophosphoric acid esters of norbornene reactants are disclosed as possessing good insecticidal, fungicidal and miticidal properties. It is also disclosed that these compounds have properties rendering them useful as corrosion inhibitors, plasticizing agents, lubricating oil additives and flotation agents, etc.

U.S. Pat. No. 3,962,105 discloses various diesters and/or ester lactones of norbornene and norbornane systems which are useful as seal swell additives.

In U.S. Pat. No. 4,028,258, a transmission fluid is disclosed comprising an alkylene oxide adduct of a phosphosulfurized-N-(hydroxyalkyl)alkenyl succinimide.

Insecticidal alkoxy and haloalkoxyphenol-phosphinyloxy and phosphinothioloxy-1,3-isoindoledones are disclosed in U.S. Pat. No. 3,401,175.

In U.S. Pat. No. 2,644,002, dialkyldithiophosphoric acid esters of succinimides are disclosed as being adaptable for various uses such as insecticides, fungicides, plasticizers, corrosion inhibitors, flotation agents, and petroleum additives.

Diesters of 1,3-bis(carboxymethyl)adamantanes which are useful as oiling agents for synthetic fibers as a synthetic lubricating oil bases are disclosed in U.S. Pat. No. 3,849,473.

None of the foregoing disclosures teach the norbornyl dialkyldithiophosphoric acid adducts of the present invention utilized as extreme pressure agents and antiwear agents for functional fluids to be used in internal combustion engines and the machinery of a motorized vehicle.

SUMMARY OF THE INVENTION

In accordance with the present invention, novel reaction products of O,O-dialkyldithiphosphoric acids with norbornene-containing reactants have been discovered which have excellent activity as extreme pressure and antiwear agents.

Further, in accordance with the present invention, functional fluids, e.g., lubricants and fuels comprising and extreme pressure and/or antiwear effective amount of the reaction products of the present invention are provided.

Still further in accordance with the invention, additives and concentrates comprising a diluent/solvent and one or more of the norbornyl-containing reaction products of the present invention are provided for formulating with functional fluids.

Still further in accordance with the present invention, a method for improving the load bearing characteristics of functional fluids used in motorized vehicles is provided.

These and other aspects of the invention will become clear to those skilled in the art upon the reading and understanding of the specification.

DETAILED DESCRIPTION OF THE INVENTION

The norbornyl dialkyldiothiophosphate adducts of the present invention may be represented by the following formula:

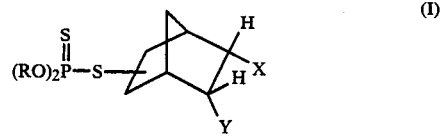

wherein R is, independently, alkyl or aryl and X and Y are the same or different and are hydrogen, carboxy, hydrocarbyl, carboxy, cyano, aldehyde, hydrocarbyl, keto N-substituted carboxamide, thio- or dithiocarbamate, thioamide, thio acid or ester, a hydrocarbyl phosphorus-containing radical, together are dicarboxylic anhydride or imide or N-hydrocarbyl-substituted imide, provided that X and Y are not both hydrogen.

As used herein, the terms "hydrocarbyl" or "hydrocarbon-based" denote a radical having a carbon atom directly attached to the remainder of the molecule and having predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical). Such radicals are known to those skilled in the art; examples include, but are not limited to, methyl, ethyl, butyl, hexyl, octyl, decyl, dodecyl, tetradecyl, octadecyl, eicosyl, cyclohexyl, phenyl and naphthyl (all isomers being included).

(2) substituted hydrocarbon radicals; that is, radicals containing non-hydrocarbon subsitutents which, in the context of this invention, do not alter the predominantly hydrocarbon character of the radical. Those skilled in the art will be aware of suitable substituents (e.g., halo, hydroxy, alkoxy, carbalkoxy, nitro, alkylsulfoxy, mercapto, alkylthio, phosphono).

(3) Hetero radicals, that is, radicals which, while predominantly hydrocarbon in character within the context of this invention, contain atoms other than carbon atoms. Suitable hetero atoms will be apparent to those skilled in the art and include, for example, nitrogen, oxygen and sulfur.

Terms such as "alkyl-based radical," "aryl-based radical" and the like having meaning analogous to the above with respect to alkyl and aryl radicals and the like.

The radicals are usually hydrocarbon and especially lower hydrocarbon, the word "lower" denoting radicals containing up to ten (10) carbon atoms. They are preferably lower alkyl or aryl radicals, most often alkyl.

The preparation of the norbornyl reactant most preferably used to react with the dialkyldithiophosphoric acid, i.e., 5-norbornene-2,3-dicarboxylic anhydride is described in Onishchenko, *Diene Synthesis* (translation from the Russian by Israel Program for Scientific Translations, Jerusalem, 1964), Daniel Davy and Company, Publisher, New York (1964), pages 38, 47, 48–50 and references cited therein. In general, the preparation of 5-horbornene-2,3-dicarboxylic anhydride involves the Diels-Alder reaction of dicyclopentadiene with maleic anhydride. All isomer forms of the reaction products of the present invention are intended to be within the scope of this invention. For example, the above-referenced process may result in the production of both the exo and endo forms of this molecule. Both isomers are intended to be within the scope of the present invention.

The above norbornene dicarboxylic anhydride reactant is then reacted with a O,O-dialkyldithiophosphoric acid of the formula:

(RO)$_2$P(S)SH to form a norbornyl dialkydithiophosphate, the structure of which may be represented by the following formula:

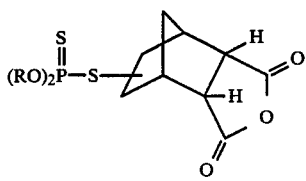

(II)

The alkyl grup R of the dithiophosphoric acid ester may contain 1 to about 30 carbon atoms and preferably 3 to about 12 carbon atoms. As previously discussed, the anhydride group on the norbornyl ring may be in the endo or exo position or there may be mixtures thereof.

The above compound (represented by formula II) may be used as an additive for functional fluids. However, it is preferable to further react this compound with another reagent in order to enhance the properties desired to give a product represented by formula I.

Thus, II above may be reacted with various hydrocarbyl containing hydroxy, thiol, alkoxy, halo and the like reactants, as well as with basic salts, to yield products represented by the general formula I.

X and Y of formula I, independently, may be a primary or secondary C$_2$ to C$_{200}$ alkyl, aralkyl, aryl or alkylaryl (linear or branched), and may contain unsaturation, halogen or heteroatoms, alicyclic or heterocyclic rings, fused rings. It may also have pendant or incorporated functionality such as —OH, —NR$_2$, carbonyl in a diversity of structures (ester, carboxylic acid, aldehyde, ketone, amide or imide), corresponding thiocarbonyl moieties, (thioesters, thiolesters, dithioesters, thio- and dithiocarbamates), halogen, alkoxy-, alkylthio, mercapto, phosphate, phosphite, phosphonate, dithiophosphate and/or phosphoramide moieties.

The half-ester acids may be used directly, or they may be converted to salts of metals selected from Group IA and IIA of the periodic table, as well as from the various transition series; which include Zn, Cd, Sn, Pb, Sb, Cu, Ni, Mn, Co, Fe, Cr, Ti and Zr, also the lanthanides, and the complex uranyl cation, UO$_2^{+2}$.

Hydrolysis of the anhydride ring of structure II produces a dicarboxylic acid which may be oleophilic depending on the size and nature of the hydrocarbyl groups of the dithiophosphate ester portion of the molecule. Alternatively, this hydrolysis product may be hydrophilic if the hydrocarbyl groups of the dithiophosphate ester are lower alkyl. The hydrophilic product may be rendered water soluble by forming the corresponding salts of Group I and II metals, as well as salts of many of the metals discussed above.

Salts of I may be made more soluble in oil or in aqueous solution by using appropriate alkyl (R) groups, and by amine complexation, where this is feasible (as with transition metal ions).

The above compounds may be prepared, in general, by reacting the particular reagent, e.g., an alcohol, an amine, an ester, a thiol or the like, with the anhydride II intermediate at an elevated temperature to obtain the desired product. For example, a monoester of II wherein Y in formula I is an acid group and X is an ester group may be prepared as illustrated below.

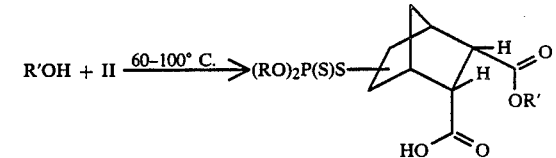

wherein R and R' are independently hydrocarbyl.

Diesters of II may be prepared, for example, by condensing II with two moles of alcohol, R'OH, generally using an acidic catalyst, such as methanesulfonic acid or p-toluenesulfonic acid.

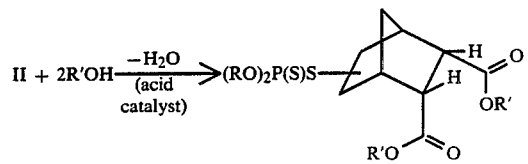

wherein R' and R are independently hydrocarbyl.

It should be noted that a mixture of different alcohols may be used to give desired solubility and other properties.

Other than the carboxylic, keto, and aldehyde reaction products illustrated above, nitrogen, sulfur and phosphorus-containing derivatives are also within the scope of the present invention. In other words, where X and Y of formula I above are amide, urethane, thioamide, thioester, dithioester, mercapto, hydrocarbyl containing dithiocarbanate, phosphate, phosphite, phosphonate, dithiophosphate and/or phosphoramide or together are imide or N-hydrocarbyl substituted imide.

These heteroatom products may be derived from hydrocarbyl amines and amides; hydrocarbyl thiols; phosphorus containing alcohols, ester and carbonates; hydrocarbyl alcohols; hydrocarbyl carbonates; hydrocarbyl carboxylic acids, anhydrides and ester; and hydrocarbyl halides.

It should be recognized that the end of the present invention represented products by formula (I) and species thereof may be prepared directly by reaction with the anhydride represented by formula (II) with the above discussed reactants or is a multiple step reaction which includes first reacting the anhydride of formula with another reagent, e.g., water followed by reaction with one or more of the above etc.

More specifically, the reagents that may be used to react with II include alkyl, aryl, alkenyl and heterocyclic amines such as methylamine, dimethylamine, amiline and subsituted amilines, aminotriazoles, aminothiazoles, aminophenols, ethanolamine, diethanolamine, triethanolamine, morpholine, stearylamine, oleylamine, palmylamine, lauryl-amine, eicosylamine, and the like; alkyl and alkenyl phosphites, phosphates and phosphonates such as hydroxy-methyl dibutyl phosphonate; alcohols such as ethanol, butanol, phenol, ethylene glycol, pentarylthritol as well as alkoxylated phenols, alkoxylated alcohols, alkoxylated amines, and the like; thiols such as ethanethiol, octanethiol, butanethiol and the like.

Where the specific reagent is a primary amine of formula "R'NH$_2$", reaction with the anhydride of structure II would be expected to produce first an amidic acid of structure I, wherein X and Y are, respectively, —CO$_2$H and —C(O)NHR. Heating this product at moderate temperatures (e.g., approximately 85° to 135° C.), causes the amidic acid to cyclize to the five-membered cyclic imide illustrated below

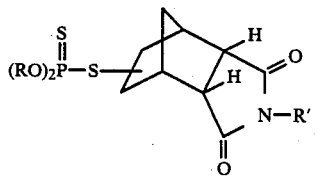

(III)

where R and R' are, independently, hydrocarbyl.

The exo or endo forms of the anhydride of formula II will form the corresponding exo or endo forms of the imides of formula III, providing that the compounds are not heated to extraordinarily high temperatures (i.e., greater than 160° C.).

Other reagents known in art that fall within the above generic categories are intended to be within the scope of this invention, where as the above-listed specific reagents are presented for illustrative purposes only.

The reaction of the above-listed reagents with the norbonyl anhydride (II) is conducted under condensation conditions recognized in the art as discussed above to illustrate the preferred method for the preparation of the monoester, diester and other such derivatives. In general, the reaction is carried out in the presence of an acid or basic catalyst and/or at an elevated temperature. The product produced may otherwise be described as the reaction product of:
(A) 5-norbornene-2,3-dicarboxylic anhydride; and
(B) O,O-dialkyldithiophosphoric acid.
The above reaction product may then, as discussed above, further be reacted with an excess of a reactant (C) which contains a group reactive with the anhydride group of (A) or the (A)(B) adduct such that the reaction product is substantially monomeric. By monomeric, it is intended that the reaction is carried out such that the final reaction product contains substantially more to a minor amount of dimer and higher polymer products. Alcohols are the preferred reactants, with alkylene glycols being the most preferred, particularly ethylene glycol.

Other alternative approaches to preparing the structures described above, which are depicted in formula I and II, are also feasible and in some instances may be more desirable for the preparation of certain of the structures which may contain specific groups. One such other method for preparing esters, half-esters, amidic acids or imides is to first form the corresponding esters, half-esters, amidic acids or imides of 5-norbornene-2,3-dicarboxylic anhydride, itself, followed by the reaction of the residual olefinic site with an O,O-dialkyl dithiophosphoric acid to form the desired saturated adducts.

The preparation of specific norbornyl compounds within the scope of the present invention is illustrated in the following examples. While these examples will show one skilled in the art how to operate within the scope of this invention, they are not to serve as a limitation on the scope of the invention where such scope is defined only in the claims. It is pointed out that in the following examples and elsewhere in the present specification and claims, all percentages and all parts are intended to express percent by weight and parts by weight unless otherwise clearly indicated.

EXAMPLE 1

Preparation of Adduct of Dialkylthiophosphoric Acid and 5-Norbornene-2,3-Dicarboxylic Anhydride A reaction flask was charged with 911 grams of 5-norbornene-2,3-dicarboxylic anhydride and 750 ml of toluene, heated to 70° C. to effect dissolution. After purging the system with inert nitrogen gas, 1980 grams of O,O-di-isoctyl dithiophosphoric acid was added in a continuous manner at 80°-90° C. over a period of 2 hours. The homogeneous solution was held at 90° C. for an additional 5 hours with stirring under a slow nitrogen sparge, during which time the strong acid number (bromophenol blue indicator) of the reaction mixture decreased rapidly.

The solution was then vacuum-stripped to 90°-100° C./5 torr, and filtered through a thin pad of diatomaceous earth to give 2723 grams (94% yield) of clear amber adduct (structure II; Risooctyl) having a bromphenol blue acid number of 2.6. The infrared spectrum of the liquid showed absorptions at 1780 and 1860 cm$^{-1}$, indicative of 5-membered cyclic anhydride. Analysis: %S=11.4; %N=5.96.

EXAMPLE 2

Reaction of the Product of Example 1 with N-Tallow-1,3-Diaminopropane

To a solution of 684 grams of the adduct of O,O-di-isooctyl dithiophosphoric acid and 5-norbornene-2,3-dicarboxylic anhydride (the product of Example 1) in 300 ml of toluene was added 420 grams of N-tallow-1,3-diaminopropane ("Duomeen T" from Armak Chemical Co.). The mixture was stirred rapidly and heated to reflux under a slow nitrogen sparge while water was removed by azeotropic distillation. After 3.8 hours, water removal was judged to be complete, and the reaction mixture was vacuum-stripped at 100° C./5 torr. Filtration through a diatomaceous earth pad give 1040 grams of dark amber liquid (96% yield). Analysis: %S=7.15; %N=3.10.

EXAMPLE 3

Alternative Process for Preparation of Imide Derivatives

A reaction flask was charged with 328 grams of 5-norborene-2,3-dicarboxylic anhydride and 300 ml of toluene. The solution was stirred under nitrogen while 258 grams of N-octylamine was added slowly. The exothermic reaction heated the solution to 95° C., at which time heat was applied and the mixture was taken to gentle reflux. Water was removed over a 2.5-hour period, and the solution was vacuum-stripped to 170° C./90 torr to give the N-octyl-5-norbornene-2,3-dicarboximide intermediate.

After cooling the imide to 95° C., 552 grams of O,O-di-(isobutyl/amyl mixed alkyl)dithiophosphoric acid was added over a 30-minute period. The reaction mixture was held at 95° C. for an additional 3 hours, during which time the acid number (bromophenol blue indicator) decreased to 5.0. The mixture was then treated with 5.0 grams of propylene oxide to further reduce the acid number to 1.0. The product was a clear amber fluid. Analysis: %S=11.77; %N=2.17; %P=5.01.

EXAMPLE 4

Reaction of the Product of Example 1 With Ethanolamine

A reaction flask was charged with 570 grams of the product of Example 1 and 300 ml of toluene. The mixture was stirred under nitrogen while 61 grams of ethanolamine was added to the solution. The temperature rose rapidly from 25° C. to 60° C. over 6 min. The solution was heated at gentle reflux (ca 110° C.) for 3 hours while 16.2 ml of water (90% of theory) was collected.

The reaction mixture was vacuum-stripped to 110° C./7 torr to provide 600 grams of amber oil. Analysis: %S=10.36. The infrared spectrum showed absorption characteristic of cyclic 5-membered imide at 1710 and 1775 cm$^{-1}$.

EXAMPLE 5

Reaction Product of Dibutyl Hydroxymethylphosphonate With the Product of Example 1

A reaction flask was charged with 358 grams of the anhydride product of Example 1 and 142 grams of dibutyl hydroxymethylphosphonate, previously prepared by base-catalyzed condensation of paraformaldehyde and dibutyl hydrogen phosphite. The reaction mixture was stirred under nitrogen, and heated in stages: 85° C. for 2 hours; 100° C. for 2 hours; 120° C. for 2.5 hours. The mixture was filtered through diatomaceous earth to give 480 grams of product. Analysis %S=6.5; %P=8.8.

EXAMPLE 6

Reaction Product of Ethylene Glycol With the Product of Example 1

A reaction flask was charged with 489 grams of the product of Example 1, 400 ml of toluene, 160 grams of ethylene glycol, and 1 gram of p-toluenesulfonic acid catalyst. The reaction mixture was stirred and heated to gentle reflux with slot nitrogen sparging, and water of condensation was removed over a period of 8 hours; a total of 16.6 ml of water was evolved at this point (100% of theory) for the formation of a diester of the cyclic dicarboxylic anhydride. The reaction mixture was cooled to room temperature and washed with two-500 ml portions of water. The toluene solution was then vacuum-stripped at 110° C./15 torr and filtered through a pad of diatomaceous earth to give 590 grams of clear yellow, viscous oil. Analysis: %S=10.00; acid number=10 (phenolphthalein indicator). The product had an H$_2$S stability, on treatment with water at 100° C., greater than 8 hours.

EXAMPLE 7

Reaction of Pentaerylthritol and the Anhydride Product of Example 1

1140 grams of the adduct of Example 1, 272 grams of pentaerythritol and 300 ml of toluene were heated under gentle reflux with rapid stirring under nitrogen for 12 hours.

The reaction mixture was vacuum stripped to 115° C./10 torr, and the residue was filtered through cloth and diatomaceous earth to give 1350 grams (96% yield) of viscous liquid product having an acid number (phenolphthalein indicator) of 65. Analysis: %S=10.20; %N=5.02. The infrared spectrum showed ester bands at 1730 cm$^{-1}$ and free CO$_2$H absorption at 1710 cm$^{-1}$.

EXAMPLE 8

O,O-Di-(Isobutyl/Amyl Mixed Alkyl)Dithiophosphoric Acid Adduct of Butyl 5-Norbornene-2-Carboxylate Dicyclopentadiene was thermally decomposed, and a 198 gram portion of freshly prepared cyclopentadiene monomer was added with rapid stirring to 384 grams of butyl acrylate, containing 2.0 grams of suspended aluminum chloride catalyst, at room temperature. The temperature was then raised to 50° C., maintained there for 1 hour, and the solution was allowed to cool overnight. Toluene was added, and the catalyst was removed by water-washing. The solution was dried over anhydrous sodium sulfate and distilled through a 1"×10" glass helix-packed column, to give 480 grams of butyl 5-norbornene-2-caboxylate, b.p. 66°-70° C./0.4 torr.

To 194 grams of this ester, with rapid stirring under a slow nitrogen sparge, was added 290 grams of O,O-(isobutyl/amyl mixed alkyl)dithiophosphoric acid. The reaction mixture was held at 50° C. for several hours, then washed once with sodium bicarbonate solution and stripped at 85° C./3 torr, and filtered through diatomaceous earth to give 411 grams of adduct. Analysis: %S=14.75; %P=6.63; acid number (bromphenol blue indicator)=nil.

EXAMPLE 9

O,O-Di-Isooctyl Dithiophosphoric Acid Adduct of 5-Norbornene-2-Carbonitrile

With rapid stirring, 132 grams of freshyl-prepared cyclopentadiene monomer was added to 106 grams of commercial acrylonitrile during 15 minutes at 40° C. The reaction mixture was stirred overnight at room temperature, then vacuum-distilled to give a 213-gram fraction (89% yield) of the desired 5-norbornene-2-carbonitrile, as a colorless liquid, b.p. 65°-69° C./4.5 torr.

At 90° C., 360 grams of O,O-di-isooctyl dithiophosphoric acid is then added to 119 grams of this carbonitrile intermediate over a 30-minute period with rapid stirring. After 3 hours at 90° C., the reaction mixture is stripped at 110° C./20 torr, and filtered to give a mobile liquid adduct.

EXAMPLE 10

O,O-Di-(Isobutyl/Amyl Mixed Alkyl)Dithiophosphoric Acid Adduct of Norbornene A flask was charged with molten bicyclo-(2.2.1) heptene-2("norbornene"), and 198 grams of O,O-di-isooctyl dithiophosphoric acid was added rapidly dropwise at 75° C. (exothermic) under nitrogen, with good stirring. The mixture was then stirred at 95° C. for 4 hours, cooled to 50° C., washed with three portions of aqueous sodium bicarbonate, and dried over anhydrous sodium sulfate, and vacuum-stripped at 100° C./2 torr. Filtration gave 213 grams (81% yield) of clear, dark amber fluid. Analysis: %S=18.49; %P=7.76; acid number (bromphenol blue indicator)=nil.

The compounds of the present invention have been found to be useful extreme pressure agents and antiwear agents as well as antioxidants for lubricating compositions. The compounds of the present invention may also find use as additives for other such functional fluids as automatic transmission fluids and hydraulic fluids.

The compounds of the invention may be formulated with a lubricating oil or an automatic transmission fluid or the like by the direct blending of the composition with the particular oil or functional fluid to be formulated. The lubricating oil or other functional fluid may also be formulated with compounds of the present invention in the form of a concentrate. Such a concentrate may be prepared by adding 1% to about 99% by weight of at least 1 compound of the present invention to a substantially iner, normally liquid organic diluent or solvent such as benzene, toluene, xylene, petroleum naphtha, mineral oil, ethyleneglycol-mono-methylether or the like.

The amount of these additives formulated with a particular lubricant may vary of a wide range and must be an amount to effectively impart extreme pressure and antiwear properties in the lubricant. As a preferred amount, the additive may range from 0.01 weight percent to about 10 weight percent of the formulated lubricant. In a most preferred embodiment, the amount may range from about 0.1 weight percent to about 5 weight percent of the formulated lubricant.

The compositions of the present invention formulated with the particular functional fluid may contain other additives and chemistries such as dispersants, antioxidants, and the like. Such other additives and chemistries include, for example, detergents and dispersants of the ash-producing or ashless type, corrosion- and oxidation-inhibiting agents, pour point depressing agents, auxiliary extreme pressure agents, color stabiliziers and antifoam agents. These other additives and chemistries are fully described and disclosed in U.S. Pat. No. 3,541,012; U.S. Pat. No. 3,697,428; and U.S. Pat. No. 4,234,435. The disclosures of these patents relating to such other additives and chemistries are hereby incorporated by reference for such disclosures.

A preferred dispersant according to the present invention is at least one substituted succinic acid or derivative thereof consisting of substitutent groups wherein the substitutent groups are derived from polyalkylene, said polyalkylene being characterized by a Mn value of 500 to about 10,000 and Mw/Mn value of 1.0 to about 4.0.

It has also been found that the additive compounds of the present invention are useful in formulating various grease compositions. The norbornene adduct additives of the present invention are useful in both mineral and synthetic lubricating oils and greases. Synthetic oils include polyolefin oils (e.g., polybutene oil, decene oligomer, and the like), synthetic esters (e.g., dinoyl sebacate, trioctanoic acid ester of trimethylolpropane, and the like), polyglycol oils, and the like. Greases are made from these oils by adding a thickening agent such as sodium, calcium, lithium, or aluminum salts of fatty acids such as stearic acid. The oils and greases of the present invention are prepared by blending an amount of the carbamate additive of the present invention sufficient to impart extreme pressure properties and antiwear properties into the oil or grease. A useful concentration may range from about 0.1 to about 5 weight percent.

To further illustrate various functional fluid compositions, specifically lubricant compositions, comprising the compositions of the present invention, the following illustrative examples are provided. It is again pointed out that the following examples are provided for illustrative purposes only and are not to place any limitation on the scope of the invention where such scope is set out only in the claims. All parts and percentages are by weight.

Typical compositions according to this invention are listed in the following table.

TABLE I

| COMPONENTS | A | B | C | D | E | F |
|---|---|---|---|---|---|---|
| Base Oil | 90.37 | 90.87 | 92.82 | 95.0 | 81.13 | 83.18 |
| Product of Example 4 |  |  |  |  |  | 2.00 |
| Product of Example 5 | 0.11 | 0.11 | 3.86 | 2.50 |  |  |
| Product of Example 6 |  |  |  |  | 2.60 |  |
| Reaction Product of Polybutenyl Succinic Anhydride with Ethylene Polyamine |  |  |  |  | 3.61 | 2.50 |
| Reaction Product of Polybutenyl Succinic Anhydride with Ethylene Polyamine and Pentaerythritol |  |  |  |  |  | 2.50 |
| Reaction Product of Polybutenyl Succinic Anhydride with Ethylene Polyamine and Carbon Disulfide | 2.00 | 2.00 |  |  |  |  |
| Reaction Product of Polybutenyl Succinic Anhydride with Ethylene Polyamine and Boric Acid | 1.00 | 1.00 |  |  |  |  |
| Basic Calcium Alkylbenzene-sulfonate | 1.79 | 1.79 |  |  |  | 1.10 |
| Basic Magnesium Alkylbenzene-sulfonate |  |  |  |  | 1.35 | 0.65 |
| Reaction Product of Maleic Anhydride-styrene Copolymer with Alcohol and Amine | 3.50 | 3.50 | 1.11 |  | 0.20 |  |
| Hydrogenated Styrene-diene Block Copolymer Viscosity Improver |  |  |  |  | 9.00 |  |
| Ethylene-propylene Copolymer Viscosity |  |  |  |  |  | 7.00 |

TABLE I-continued

| COMPONENTS | A | B | C | D | E | F |
|---|---|---|---|---|---|---|
| Improver | | | | | | |
| Sulfurized Fat | 0.50 | | | | | |
| Reaction Product of an Organo Sulfur Cmpd. with an Epoxide | 0.50 | 0.50 | | | | |
| Sulfurized Olefin | | | | 2.50 | 1.50 | |
| Ester of Dimercaptothiadiazole | | | 0.17 | | 0.10 | 0.06 |
| Sulfurized Diels-Alder Adduct | | | | | | 0.60 |
| Oil Soluble Phosphorus-Containing Extreme Pressure Agent | | | 1.47 | | | |
| Alkylated Arylamine | 0.10 | 0.10 | | | 0.50 | 0.30 |
| Ethoxylated Fatty Amine | 0.09 | 0.09 | | | | |
| Fatty Amide | | | 0.11 | | | 0.10 |
| Fatty Amine | | | 0.39 | | | |
| Silicone Antifoam Agent | 0.042 | 0.042 | 0.066 | | 0.006 | 0.006 |

The products of the various examples, contained in a fully formulated lubricating composition as is described in Table I, were then tested with regard to a Timken "OK" load test as well as a contact pressure test in accordance with ASTM D 2782 with the exception that in the "OK" load test the following procedural differences were made:

1. Test cup and block surfaces are merely "wetted" with test lubricant (approximately 5 drops on lock). No test sample is recirculated over the surfaces during the test.
2. Test duration is 5 minutes under load.
3. This procedure is run as an "OK" Load test, determining "OK" Load as in ASTM Test D 2782 except utilizing the following load increments:
   a. "OK" Load is less than or equal to 20 lbs.: Determine "OK" Load to the nearest 1 lb.
   b. "OK" Load is greater than 20 lbs.: Determine "OK" Load using standard load increments as described in ASTM Test D 2782.

The results from testing products of the present invention according to the above test procedures are set out in Table II below.

TABLE II

| Compound | Timken Results # Loading | Unit Pres. psi | Wt %[2] Chem |
|---|---|---|---|
| Product of Example 2 | 16 | 12,500 | 1.46 |
| Product of Example 3 | 23 | 15,550 | 1.0 |
| | 28 | 16,725 | 2.0 |
| Product of Example 4 | 18 | 13,050 | 1.0 |
| Product of Example 6 | 25 | 10,300 | 1.12 |
| Product of Example 7 | 16 | 6,025 | 1.0 |
| Zn O,O—di(iso-[1] buty/amyl mixed alkyl)dithiophosphate | 17 | 7,000 | 0.52 |

[1]Comparison - a typical antiwear agent
[2]Percent weight of the product in the fully formulated oil; all samples evaluated at 0.05% P, as experimental product The invention also includes aqueous compositions characterized by an aqueous phase with at least one amine and/or metal salt of at least one dimer of polymer of the present invention dispersed or dissolved in said aqueous phase. Preferably, this aqueous phase is a continuous aqueous phase although, in some embodiments, the aqueous phase can be a discontinuous phase. These aqueous compositions usually contain at least about 25% by weight water. Such aqueous compositions encompass both concentrates containing about 25% to about 80% by weight, preferably from about 40% to about 65% water; and water-based functional fluids containing generally greater than about 80% by weight of water. The concentrates generally contain from about 10% to about 90% by weight of at least one of the norbornene adduct additives of the invention. The water-based functional fluids generally contain from about 0.05% to about 15% weight of the norbornene adduct materials of the invention. The concentrates generally contain less than about 50%, preferably less than about 25%, more preferably less than about 15%, and still more preferably less than about 6% hydrocarbon oil. The water-based functional fluids generally contain less than about 15%, preferably less than about 5%, and more preferably less than about 2% hydrocarbon oil.

These concentrates and water-based functional fluids can optionally include other conventional additives commonly employed in water-based functional fluids. These other additives include surfactants; thickeners; oil-soluble, water-insoluble functional additives such as antiwear agents, extreme pressure agents, dispersants, etc.; and supplemental additives such as corrosion-inhibitors, shear stabilizing agents, bactericides, dyes, water-softeners, odor masking agents, anti-foam agents and the like.

The concentrates are analogous to the water-based functional fluids except except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily be ease of handling the convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbon oil.

In various preferred embodiments of the invention, the water-based functional fluids are in the form of solutions while in other embodiments they are in the form of micelle dispersions or microemulsions which appear to be true solutions. Whether a solution, micelle dispersion or microemulsion is formed is dependent, inter alia, on the particular components employed.

Also included within this invention are methods for preparing aqueous compositions, including both concentrates and water-based functional fluids, containing other conventional additives commonly employed in water-based functional fluids. These method comprise the steps of:

(1) mixing at least one norbornene adduct additive of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the components of the invention and other functional additives in said concentrates or said water-based functional fluids.

These mixing steps are preferably carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances, the finished water-based functional fluid can be formed directly in the same equipment used to form the concentrate or the dispersion or solution.

The surfactants that are useful in the aqueous compositions of the invention can be of the cationic, anionic, nonionic or amphoteric type. Many such surfactants of each type are know to the art. See, for example, McCutcheon's "Emulsifiers & Detergents," 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable nonionic surfactants are known; see, for example, the aforementioned McCutcheon's as well as the treatise "Non-Ionic Surfactants" edited by Martin J. Schick, M. Dekker Co., New York, 1967, which is herein incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants," Parts II and III, edited by W. M. Linfield, published by Marcel Dekker, Inc., New York, 1976, and "Cationic Surfactants," edited by E. Jungermann, Marcel Dekker, Inc., New York, 1976. Both of these references are incorporated by reference for their disclosures in this regard.

These surfactants, when used, are generally employed in effective amounts to aid in the dispersal of the various additives, particularly the functional additives discussed below, in the concentrates and water-based functional fluids of the invention. Preferably, the concentrates can contain up to about 75% by weight, more preferably from about 10% to about 75% by weight of one or more of these surfactants. The water-based functional fluids can contain up to about 15% by weight, more preferably from about 0.05% to about 15% by weight of one or more of these surfactants.

Often the aqueous compositions of this invention contain at least one thickener for thickening said compositions. Generally, these thickeners can be polysaccharides, synthetic thickening polymers, or mixtures of two or more of these. Among the polysaccharides that are useful are natural gums such as those disclosed in "Industrial Gums" by Whistler and B. Miller, published by Academic Press, 1959. Disclosures in this book relating to water-soluble thickening natural gums in hereby incorporated by reference. Specific examples of such gums are gum agar, guar gum, gum arabic, algin, dextrans, xanthan gum and the like. Also among the polysaccharides that are useful as thickeners for the aqueous compositions of this invention are cellulose ethers and esters, including hydroxy hydrocarbyl cellulose and hydrocarbylhydroxy cellulose and its salts. Specific examples of such thickeners are hydroxyethyl cellulose and the sodium salt of carboxymethyl cellulose. Mixtures of two or more of any such thickeners are also useful.

It is a general requirement that the thickener used in the aqueous compositions of the present invention be soluble in both cold (10° C.) and hot (about 90° C.) water. This excludes such materials as methyl cellulose which is soluble in cold water but not in hot water. Such hot-water-insoluble materials, however, can be used to perform other functions such as providing lubricity to the aqueous compositions of this invention.

These thickeners can also be synthetic thickening polymers. Many such problems are known to those of skill in the art. Representative of them are polyacrylates, polyacrylamides, hydrolyzed vinyl esters, water-soluble homo- and interpolymers of acrylamidoalkane sulfonates containing 50 mole percent at least of acryloamido alkane sulfonate and other comonomers such as acrylonitrile, styrene and the like. Poly-n-vinyl pyrrolidones, homo- and copolymers as well as water-soluble salts of styrene, maleic anhydride and isobutylene maleic anhydride copolymers can also be used as thickening agents.

Other useful thickeners are known to those of skill in the art and many can be found in the list in the aforementioned McCutcheon Publication: "Functional Materials," 1976, pp. 135-147, inclusive. The disclosures therein, relative to water-soluble polymeric thickening agents meeting the general requirements set forth above are hereby incorporated by reference.

Preferred thickeners, particularly when the compositions of the invention are required to be stable under high shear applications, are the water-dispersible reaction products formed by reacting at least one hydrocarbyl-substituted succinic acid and/or anhydride represented by the formula

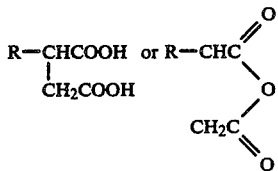

wherein R is a hydrocarbyl group of from about 8 to about 40 carbon atoms, with at least one water-dispersable amine terminated poly(oxyalkenylene) or at least one water-dispersible hydroxy-terminated polyoxyalkylene. R preferably has from about 8 to about 30 carbon atoms, more preferably from about 12 to about 24 carbon atoms, still more preferably from about 16 to about 18 carbon atoms. In a preferred embodiment, R is represented by the formula

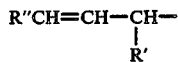

wherein R' and R" are independently hydrogen or straight chain or substantially straight chain hydrocarbyl groups, with the proviso that the total number of carbon atoms in R is within the above-indicated ranges. Preferably R' and R" are alkyl or alkenyl groups. In a particularly advantageous embodiment, R has from about 16 to about 18 carbon atoms, R' is hydrogen or an alkyl group of from 1 to about 7 carbon atoms or an alkenyl group of from 2 to about 7 carbon atoms, and R" is an alkyl or alkenyl group of from about 5 to about 15 carbon atoms.

The water-dispersible amine terminated poly(oxyalkylene)s are preferably alpha omega diamino poly(oxyethylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a urea condensate of such alpha omega diamino poly(oxytheylene)s, alpha omega diamino poly(oxypropylene) poly(oxyethylene) poly(oxypropylene)s or alpha omega diamino propylene oxide capped poly(oxyethylene)s. The amine-terminated poly(oxyalkylene) can also be a polyamine (e.g., triamino, tetramino, etc.) polyoxyalkylene provided it is amine-terminated and it is water-dispersible.

Examples of water-dispersible amine-terminated poly(oxyalkylene)s that are useful in accordance with the present invention are disclosed in U.S. Pat. Nos. 3,021,232; 3,108,011; 4,444,566; and RE 31,522. The disclosures of these patents are incorporated herein by reference. Water-dispersible amine terminated poly(oxyalkylene)s that are useful are commercially available from the Texaco Chemical Company under the trade name "Jeffamine."

The water-dispersible hydroxy-terminated polyoxyalkylenes are constituted of block polymers of propylene oxide and ethylene oxide, and a nucleus which is derived from organic compounds containing a plurality of reactive hydrogen atoms. The block polymers are attached to the nucleus at the sites of the reactive hydrogen atoms. Examples of these compounds include the hydroxy-terminated polyoxyalkylenes which are represented by the formula

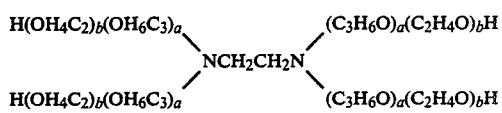

wherein a and b are integers such that the collective molecular weight of the oxypropylene chains range from about 900 to about 25,000, and the collective weight of the oxyethylene chains constitute from about 20% to about 90%, preferably from about 25% to about 55% by weight of the compound. These compounds are commercially available from BASF Wyandotte Corporation under the trade name "Tetronic." Additional examples include the hydroxy-terminated polyoxyalkylenes represented by the formula

wherein y is an integer such that the molecular weight of the oxypropylene chain is at least about 900, and x and z are integers such that the collective weight of the oxyethylene chains constitute from about 20% to about 90% by weight of the compound. These compounds preferably have a molecular weight in the range of about 1,100 to about 14,000. These compounds are commercially available from BASF Wyandotte Corporation under the trade name "Pluronic." Useful hydroxy-terminated polyoxyalkylenes are disclosed in U.S. Pat. Nos. 2,674,619 and 6,979,528, which are incorporated herein by reference.

The reaction between the carboxylic agent and the amine- or hydroxy-terminated polyoxyalkylene can be carried out at a temperature ranging from the highest of the melt temperature of the reaction components up to the lowest of the decomposition temperatures of the reaction components or products. Generally, the reaction is carried out at a temperature in the range of about 60° C. to about 160° C., preferably about 120° C. to about 160° C. The ratio of equivalents of carboxylic agent to polyoxyalkylene preferably ranges from about 0.1:1 to about 8:1, preferably about 1:1 to about 4:1, and advantageously about 2:1. The weight of an equivalent of the carboxylic agent can be determined by dividing its molecular weight by the number of carboxylic functions present. The weight of an equivalent of the amine-terminated polyoxyalkylene can be determined by dividing its molecular weight by the number of terminal amine groups present. The weight of an equivalent of the amine-terminated polyoxyalkylene can be determined by dividing its molecular weight by the number of terminal amine groups present. The number of terminal amine and hydroxyl groups can usually be determined from the structural formula of the polyoxyalkylene or empirically through well-known procedures. The amine/acids and ester/acids formed by the reaction of the carboxylic agent and amine-terminated or hydroxy-terminated polyoxyalkylene can be neutralized with, for example, one or more alkali metals, one or more amines, or a mixture thereof, and thus converted to amide/salts or ester/salts, respectively. Additionally, if these amide/acids or ester/acids are added to concentrates or functional fluids containing alkali metals or amines, amide/salts or ester/salts usually form, in situ.

South African Pat. No. 85/0978 is incorporated herein by reference for its teachings with respect to the use of hydrocarbyl-substituted succinic acid or anhydride/hydroxy-terminated poly(oxyalkylene) reaction products as thickeners for aqueous compositions.

When the thickener is formed using an amine-terminated poly(oxyalkylene), the thickening characteristics of said thickener can be enhanced by combining it with at least one surfactant. Any of the surfactants identified above under the subtitle "Surfactants" can be used in this regard. When such surfactants are used, the weight ratio of thickener to surfactant is generally in the range of from about 1:5 to about 5:1, preferably from about 1:1 to about 3:1.

Typically, the thickener is present in a thickening amount in the aqueous compositions of this invention. When used, the thickener is preferably present at a level of up to about 70% by weight, preferably from about 20% to about 50% by weight of the concentrates of the invention. The thickener is preferably present at a level in the range of from about 1.5% to about 10% by weight, preferably from about 3% to about 6% by weight of the functional fluids of the invention.

The functional additives that can be used in the aqueous systems are typically oil-soluble, water-insoluble additives which function in conventional oil-based systems as extreme pressure agents, antiwear agents, load-carrying agents, dispersants, friction modifiers, lubricity agents, etc. They can also function as anti-slip agents, film formers and friction modifiers. As is well known, such additives can function in two or more of the above-mentioned ways; for example, extreme pressure agents often function as load-carrying agents.

The term "oil-soluble, water-insoluble functional additive" refers to a functional additive which is not soluble in water above a level of about 1 gram per 100 milliliters of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear," Volume 26, pages 369–392, and West German Published Patent Application No. 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Many such functional additives are known to the art. For example, descriptions of additives useful in conventional oil-based systems and in the aqueous systems of this invention are found in "Advances in Petroleum Chemistry and Refining," Volume 8, edited by John J. McKetta, Interscience Publishers, New York, 1963, pages 31–38 inclusive. Kirk-Othmer "Encyclopedia of chemical Technology," Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These refernces are hereby incorporated by reference for their disclosures of functional additives useful in the compositions of this invention.

In certain of the typical aqueous compositions of the invention, the functional additive is a sulfur or chlorosulfur extreme pressure agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of a phosphorodithioic acid, such as zinc dicyclohexyl phosphorodithioate.

The functional additive can also be a film former such as a synthetic or natural latex or emulsion thereof in water. Such latexes include natural rubber latexes and polystyrene butadienes synthetic latex.

The functional additive can also be anti-chatter or anti-squawk agent. Examples of the former are the amide metal dithiophosphate combinations such as disclosed in West German Pat. No. 1,109,302; amine salt-azomethene combinations such as disclosed in British Patent Specification No. 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Trade Name | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1] The Lubrizol Corporation, Wickliffe, Ohio, U.S.A.
[2] R. T. Vanderbilt Company, Inc., New York, New York, U.S.A.
[3] Witco Chemical Corp., Organics Division, Houston, Texas, U.S.A.

Mixtures of two or more of any of the afore-described functional additives can also be used.

Typically, a functionally effective amount of the functional additive is present in the aqueous compositions of this invention.

The term "functionally effective amount" refers to a sufficient quantity of an additive to impart desired properties intended by the addition of said additive. For example, if an additive is a rust-inhibitor, a functionally effective amount of said rust-inhibitor would be an amount sufficient to increase the rust-inhibiting characteristics of the composition to which it is added. Similarly, if the additive is an antiwear agent, a functionally effective amount of said antiwear agent would be a sufficient quantity of the antiwear agent to improve the antiwear characteristics of the composition to which it is added.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion-inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596–605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanolamine. Mixtures of two or more of any of the afore-described corrosion-inhibitors can also be used. The corrosion-inhibitor is usually present in concentrations in which they are effective in inhibiting corrosion of metals with which the aqueous composition comes in contact.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and work tool, the polyol of inverse solubility "plates out" on the surface of the workpiece, thus improving its lubricity characteristics.

The aqueous systems of the present invention can also include at least one bactericide. Such bactericides are well known to those of skill in the art and specific examples can be found in the afore-mentioned McCutcheon publication "Functional Materials" under the heading "Antimicrobials" on pages 9–20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an antifreeze additive where it is desired to use the composition at a low temperature. Materials such as ethylene glycol and analogous polyoxyalkylene polyols can be used as antifreeze agents. Clearly, the amount used will depend on the degree of antifreeze protection desired and will be known to those of ordinary skill in the art.

It should also be noted that many of the ingredients described above for use in making the aqueous systems of this invention are industrial products which exhibit or confer more than one property on such aqueous compositions. Thus, a single ingredient can provide several functions thereby eliminating or reducing the need for some other additional ingredient. Thus, for example, an extreme pressure agent such as tributyl tin oxide can also function as a bactericide.

While the invention has been described and illustrated with reference to certain preferred embodiment thereof, those skilled in the art will appreciate that various changes, modifications and substitutions can be made therein without departing from the spirit of the invention. For example, different concentration ranges other than the preferred ranges set forth hereinabove may be applicable as a consequence of variations in the oil base stock or the type of engine or the like. It is intended, therefore, that the invention be limited only by the scope of the claims which follow.

What is claimed is:

1. A lubricating composition comprising a major amount of an oil of lubricating viscosity and minor amount of a compound of the formula:

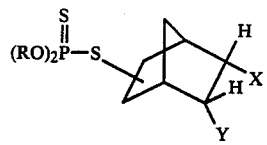

wherein R is, independently, alkyl or aryl and X and Y are independently selected from the group consisting of hydrogen, hydrocarbyl carboxy, N-substituted carboxamide, thio- or dithiocarbamate, thioamide, thio acid or ester, a hydrocarbyl phosphorus containing radical, together are imide or N-hydrocarbyl substituted imide, provided that when X is alkyl carboxy, Y is not alkyl carboxy, or hydrogen and X and Y are not both hydrogen.

2. The composition according to claim 1 wherein X and Y are independently hydroxyalkyl carboxy.

3. The composition according to claim 2 wherein X and Y are the same and are hydroxyethyl carboxy.

4. A method for improving the load bearing properties of lubricating composition of lubricating viscosity by admixing therewith a minor amount of an extreme pressure and an antiwear agent of the formula:

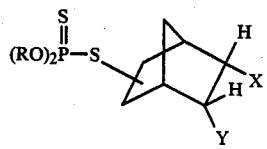

wherein R is, independently, alkyl or aryl and X and Y are independently selected from the group consisting of hydrogen, hydrocarbyl carboxy, N-substituted carboxamide, thio- or dithiocarbamate, thioamide, thio acid or ester, a hydrocarbyl phosphorus containing radical, together are imide or N-hydrocarbyl substituted imide, provided that when X is alkyl carboxy, Y is not alkyl carboxy a hydrogen and X and Y are not both hydrogen.

5. The method according to claim 4 wherein X and Y are the same and are hydroxy ethyl carboxy.

6. A compound of the formula:

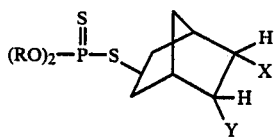

wherein R is, independently, alkyl or aryl and X and Y are independently selected from the group consisting of N-substituted carboxamide, thioamide, thioester, dithioester, hydrocarbyl-containing dithiocarbamate, hydrocarbylthio, phosphate, phosphite, phosphonate, dithiophosphate, phosphoramide, or together represent imide or are N-hydrocarbyl imide.

7. The compound according to claim 6 wherein X and Y are, independently, phosphonate, N-substituted carboxamide, or together are imide or N-hydrocarbyl imide.

8. A lubricant additive comprising the compound of claim 6.

9. A concentrate for formulating lubricating compositions comprising from about 1% to about 99% by weight of a normally liquid, substantially inert organic solvent/diluent and at least one compound of claim 6.

10. A lubricating composition comprising a major amount of an oil of lubricating viscosity and a minor amount of at least one compound of claims 6 or 7 or at least one concentrate of claim 9.

11. A method for improving the load bearing properties of a lubricating composition comprising admixing with a major amount of a lubricating composition, a minor amount of the compound or concentrate of claims 6, 7 or 9.

12. An aqueous functional fluid comprising a minor effective amount of at least one compound set out in any one of claims 1-3.

13. A grease composition comprising a minor effective amount of at least compound set out in any one of claims 1-3.

* * * * *